(12) United States Patent
Schmidt

(10) Patent No.: US 11,857,799 B2
(45) Date of Patent: Jan. 2, 2024

(54) WEARABLE SELECTIVE BIOPHOTON REFLECTOR

(71) Applicant: SOLETLUNA HOLDINGS, INC., San Diego, CA (US)

(72) Inventor: David Schmidt, San Diego, CA (US)

(73) Assignee: SOLETLUNA HOLDINGS, INC., San Diego, CA (US)

( * ) Notice: Subject to any disclaimer, the term of this patent is extended or adjusted under 35 U.S.C. 154(b) by 36 days.

(21) Appl. No.: 17/571,429

(22) Filed: Jan. 7, 2022

(65) Prior Publication Data

US 2023/0218918 A1 Jul. 13, 2023

(51) Int. Cl.
*A61N 5/06* (2006.01)
*A61N 5/073* (2006.01)

(52) U.S. Cl.
CPC ........ *A61N 5/06* (2013.01); *A61N 2005/0645* (2013.01); *A61N 2005/0657* (2013.01); *A61N 2005/0659* (2013.01); *A61N 2005/0663* (2013.01); *A61N 2005/0666* (2013.01); *A61N 2005/0667* (2013.01); *A61N 2005/073* (2013.01)

(58) Field of Classification Search
CPC .............. A61N 5/06; A61N 2005/0645; A61N 2005/0657; A61N 2005/0666; A61N 2005/0667; A61N 2005/073
See application file for complete search history.

(56) References Cited

U.S. PATENT DOCUMENTS

| 8,273,567 B2 | 9/2012 | Ko et al. |
| 10,610,513 B2 | 4/2020 | Bellini et al. |
| 11,064,919 B2 | 7/2021 | Matsui et al. |
| 11,090,475 B2 | 8/2021 | Pelkus |
| 11,103,333 B2 | 8/2021 | Khakpour et al. |

(Continued)

FOREIGN PATENT DOCUMENTS

| DE | 202008011806 U1 | * | 10/2009 | ............... A61N 5/06 |
| DE | 202018002388 U1 | * | 9/2019 | ............... A61N 5/06 |
| WO | WO-2020180653 A1 | * | 9/2020 | ............... A23L 2/50 |

OTHER PUBLICATIONS

Gupta et. al., "Effect of red and near-infrared wavelengths on low-level laser (light) therapy-induced healing of partial-thickness dermal abrasion in mice", Lasers Med Sci 2014; 29:257-265.

(Continued)

*Primary Examiner* — Carl H Layno
*Assistant Examiner* — Aya Ziad Bakkar
(74) *Attorney, Agent, or Firm* — ARC IP Law, PC; Joseph J. Mayo

(57) ABSTRACT

A wearable device that selectively reflects biophotons emitted naturally from the user's body back into the body, achieving beneficial health effects similar to low-level laser therapy without requiring an external laser device. Illustrative wavelengths that may be reflected may include 550 nm, 630 nm, 632 nm, 660 nm, 694 nm, 810 nm, and 980 nm. Radiation of wavelength 810 nm in particular has been shown to affect mitochondrial energy production. The device may be worn for example as a bracelet or pendant. Internal components may include one or more filters to select the desired wavelengths, and a parabolic mirror to reflect these selected wavelengths back into the body. Some embodiments may also include a polarizer so that reflected waves are polarized.

10 Claims, 4 Drawing Sheets

(56) References Cited

U.S. PATENT DOCUMENTS

| | | |
|---|---|---|
| 11,116,454 B2 | 9/2021 | Ishikawa |
| 11,116,841 B2 | 9/2021 | Loupis et al. |
| 11,122,996 B2 | 9/2021 | Nakazawa et al. |
| 2021/0162232 A1 | 6/2021 | Bani et al. |

OTHER PUBLICATIONS

Wang et al., "Photobiomodulation of human adipose-derived stem cells using 810nm and 980nm lasers operates via different mechanisms of action", Biochimica et Biophsica Acta General Subjects, vol. 1861, Issue 2, Feb. 2017, pp. 441-449.

Stoldt et al., "Parasite Presence Induces Gene Expression Changes in an Ant; Host Related to Immunity and Longevity", Genes 2021 (17 pages).

Srinivasan TM, "Biophotons as subtle energy carriers", Int J Yoga 2017;10 (2 pages).

Van Wijk et al., "An Introduction to Human Biophoton Emission", Forsch Komplementärmed Klass Naturheilkd 2005; 12:77-83.

* cited by examiner

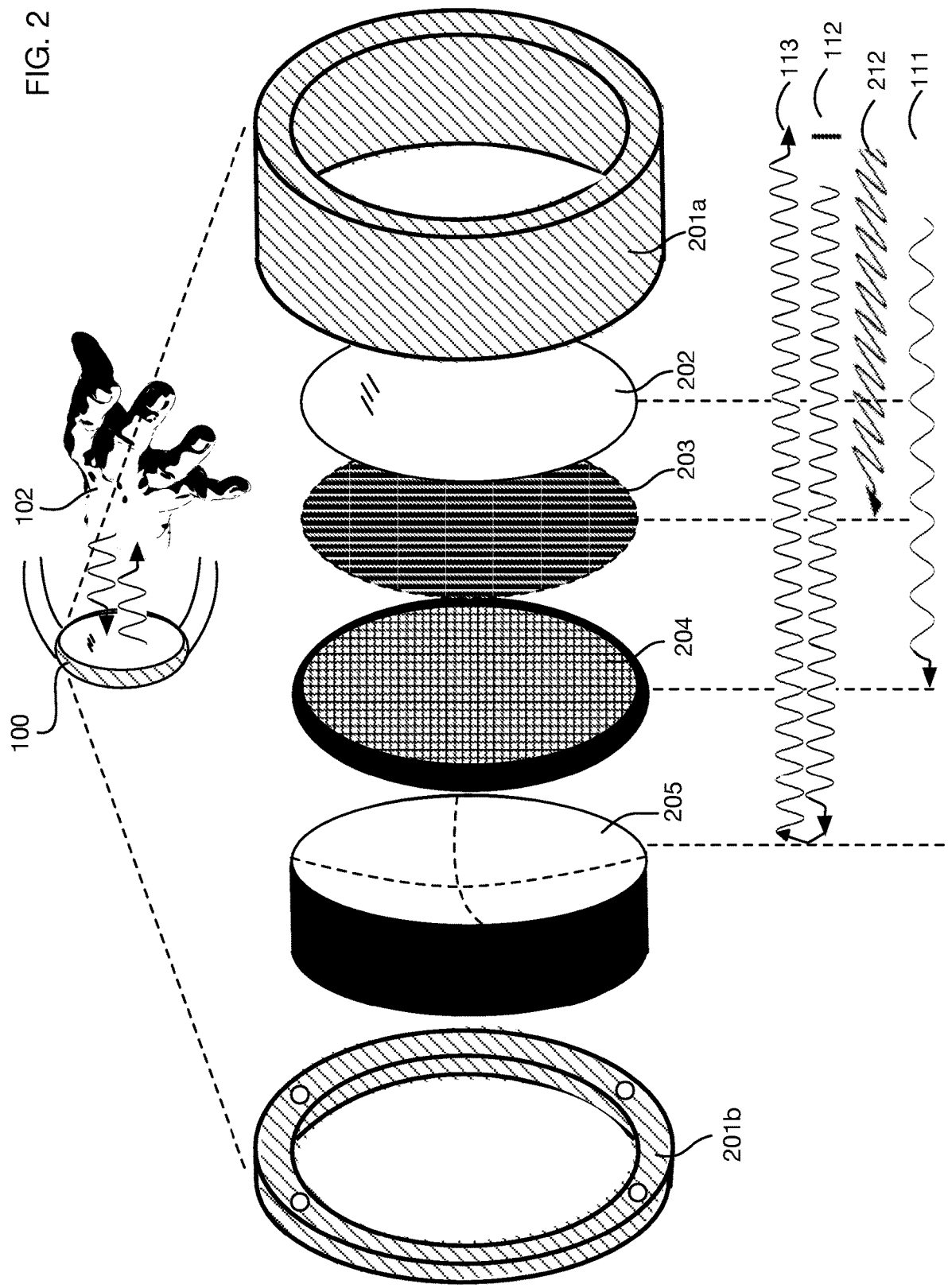

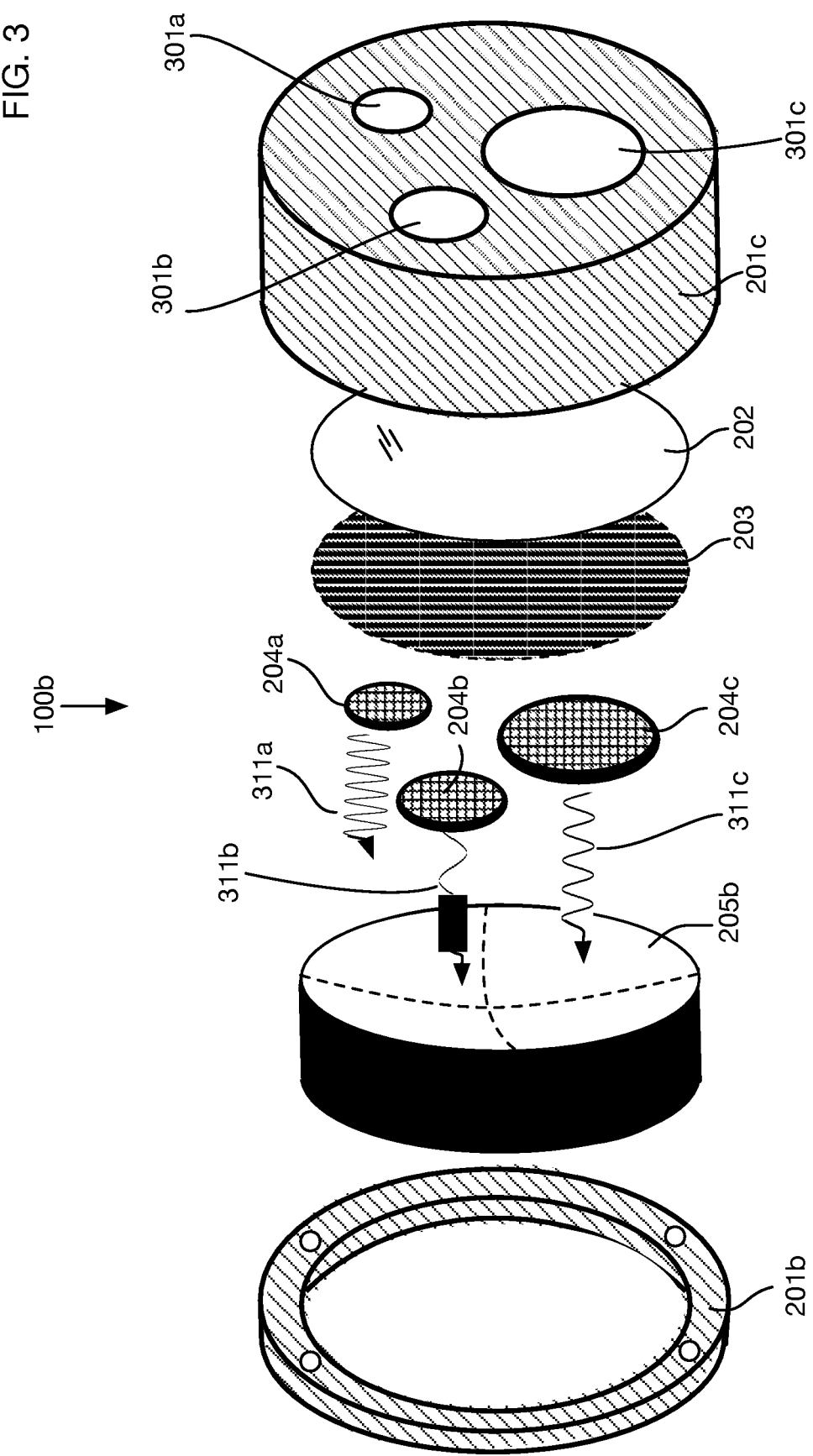

WEARABLE SELECTIVE BIOPHOTON REFLECTOR

BACKGROUND OF THE INVENTION

Field of the Invention

One or more embodiments of the invention are related to the field of wearable phototherapy devices. More particularly, but not by way of limitation, one or more embodiments of the invention enable a wearable device that selectively reflects biophotons generated by a person's body back towards the body.

Description of the Related Art

Low-level laser therapy (LLLT) has been shown to have beneficial biological effects on human subjects in several studies and in clinical practice. Studies have shown that the effects of LLLT are wavelength-dependent, and that certain wavelengths provide optimal effects. For example, Gupta et. al. in "Effect of red and near-infrared wavelengths on low-level laser (light) therapy-induced healing of partial-thickness dermal abrasion in mice" (Lasers Med Sci 2014 29:257-265) show that tissue healing of mice is significant at wavelengths of 635 nm and 810 nm, but not at wavelengths of 730 nm and 980 nm. They speculate that the greater effectiveness of 810 nm compared to 635 nm may be due to the absorption spectrum of cytochrome c oxidase, the candidate mitochondrial chromophore in LLLT. Wang et. al. in "Photobiomodulation of human adipose-derived stem cells using 810 nm and 980 nm lasers operates via different mechanisms of action" (Biochimica et Biophsica Acta General Subjects, Volume 1861, Issue 2, February 2017, pp. 441-449) similarly find a significant effect at 810 nm due to effects on mitochondrial cytochrome c oxidase and find that 980 nm affects temperature-gated calcium channels. Upregulation of genes that affect cytochrome c oxidase has been shown to dramatically increase the lifespan of ants (Stoldt et. al., "Parasite Presence Induces Gene Expression Changes in an Ant Host Related to Immunity and Longevity", Genes 2021, 12, 95), suggesting that increases in cytochrome c oxidase may have general health benefits.

Existing therapy devices using LLLT generate radiation in desired wavelengths and direct this energy towards the body. A disadvantage of these devices is that they require external power and specialized equipment. They are often prohibitively expensive for individual consumer use. An alternative approach, which is not known in the art, is to use radiation spontaneously emitted from the body, called biophoton emission, and to reflect selected wavelengths of biophotons back into the body to obtain the beneficial effects of these wavelengths. Research has shown that humans emit ultra-weak light that is linked to endogenous production of excited states within the body (Van Wijk et. al., "An Introduction to Human Biophoton Emission", Forsch Komplementärmed Klass Naturheilkd 2005; 12:77-83). Research to date has focused on measuring these biophotons, rather than on reflecting them back into the body for a beneficial effect. There are no known devices that reflect selected biophotons back into the body.

For at least the limitations described above there is a need for a wearable selective biophoton reflector.

BRIEF SUMMARY OF THE INVENTION

One or more embodiments described in the specification are related to a wearable selective biophoton reflector. Embodiments of the invention may provide a beneficial effect for the user due to reflection of selected wavelengths of naturally emitted biophotons back into the user's body. One or more embodiments of the invention may be worn against or near the skin on or near any part of the body, for example as a pendant or in a bracelet.

One or more embodiments of the invention may be worn by a subject to provide a beneficial effect for the subject. Components of the device worn by the subject may include a clear window configured to be placed near the subject's body, one or more filters behind the window, a mirror behind the filter, and a housing that holds the clear window, the one or more filters, and the mirror. The one or more filters may be configured to selectively pass one or more biologically beneficial wavelengths of biophoton radiation emitted from the body of the subject. The mirror may be configured to reflect the selected biologically beneficial wavelengths of biophoton radiation back towards the body. The wearable selective biophoton reflector may not include a power source and may not be coupled to any external power source.

In one or more embodiments the beneficial effect may include elevated energy production in the cells of the subject. It may for example include elevated energy levels of cytochrome c oxidase in the cells of the subject.

In one or more embodiments the biologically beneficial wavelengths may include one or more of 550 nanometers, 630 nanometers, 632 nanometers, 660 nanometers, 694 nanometers, 810 nanometers, and 980 nanometers.

In one or more embodiments the mirror may be a parabolic mirror. (A spherical mirror may be used as an approximation of a parabolic mirror.) The mirror may be a gold-coated mirror.

One or more embodiments may include a polarizer between the clear window and the mirror.

BRIEF DESCRIPTION OF THE DRAWINGS

The above and other aspects, features and advantages of the invention will be more apparent from the following more particular description thereof, presented in conjunction with the following drawings wherein:

FIG. 2 shows an exploded view of components of an illustrative embodiment of the invention.

FIG. 3 shows an exploded view of components of an embodiment of the invention that uses multiple filters to select multiple wavelengths.

DETAILED DESCRIPTION OF THE INVENTION

A wearable selective biophoton reflector will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1A:
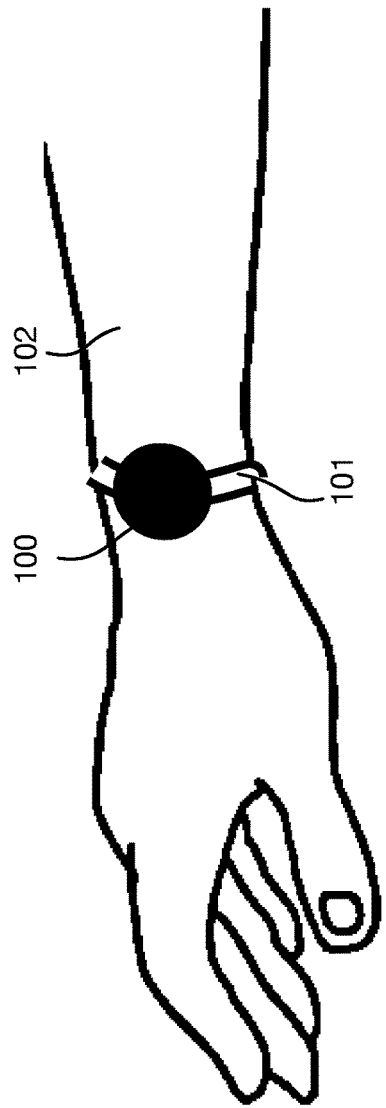
FIG. 1A shows an illustrative embodiment of the invention worn by a subject on the wrist.

FIG. 1A shows an illustrative embodiment of the invention 100, which in this example is worn by a human subject on the arm or wrist with a wristband or bracelet 101 to hold the device 100 against or near to the subject's skin 102. As described below, the side of device 100 against the skin includes a transparent window that collects biophotons emitted from the skin under the device. In one or more embodiments, the device 100 may be of any shape and size, and it may be placed on any part or parts of the body. For example, without limitation, it may be worn as a pendant (as shown in FIG. 1C) or collar, as an armband, as a band around the ankle or leg, as a headband, or it may be integrated into any article of clothing or accessory.

Device 100 may not include or require any power source or connection to external power. It may be a passive device that collects, filters, and reflects biophotons emitted from the skin 102 of the subject's body. Benefits of the lack of power source or power connection include lighter weight, lower cost, higher reliability, and much longer longevity.

Figure 1B:
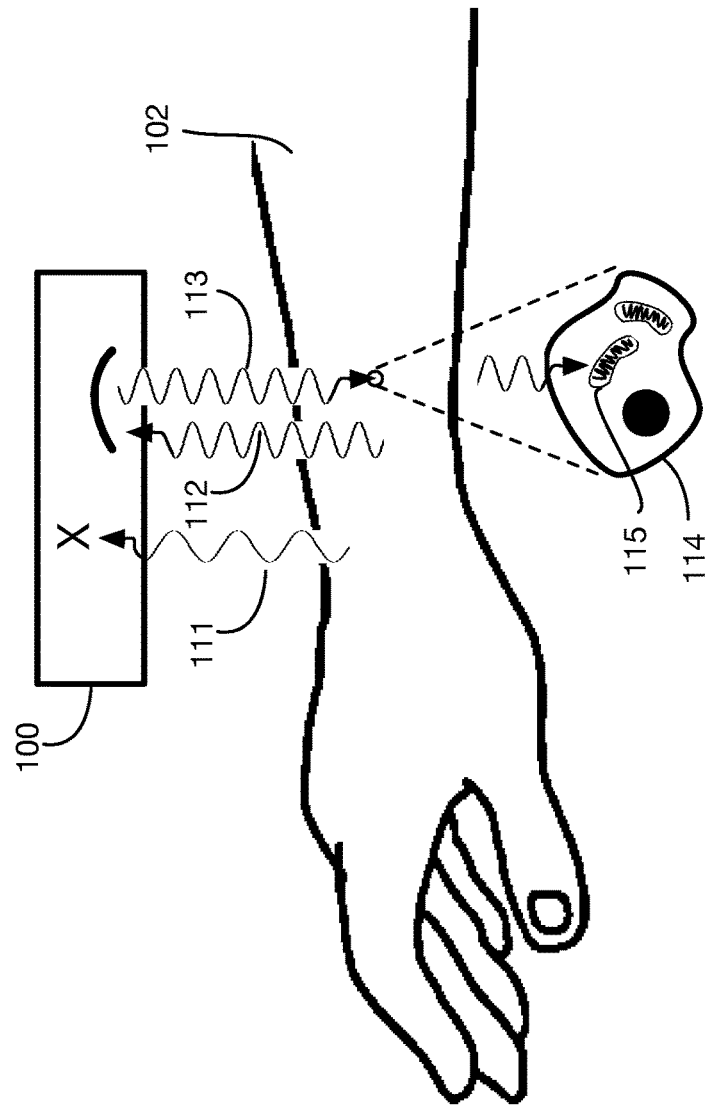
FIG. 1B shows a block diagram that illustrates the selective reflection of biophotons by the embodiment of FIG. 1A.

FIG. 1B shows a high-level architectural diagram of device 100 illustrating the interaction of the device with the biophotons emitted from subject 102. Subject 102 emits biophoton radiation of various wavelengths, including for example radiation 111 at one wavelength and radiation 112 at a different (shorter) wavelength. In this application, the device 100 is configured to reflect only a narrow band around wavelength 112, to optimize for the health benefits of that particular wavelength. Radiation 112 emitted from the skin is therefore reflected as radiation 113 that is directed back towards the skin of subject 102. Radiation 111 is not reflected. The specific wavelength or wavelengths selected for an embodiment of the invention may differ across applications. Illustrative wavelengths that may be selected for in one or more embodiments may include for example, without limitation, 550 nanometers, 630 nanometers, 632 nanometers, 660 nanometers, 694 nanometers, 810 nanometers, and 980 nanometers. The band of selected wavelengths around the desired wavelength may be for example in the range of 10 nanometers to 20 nanometers in one or more embodiments. As an example, a device configured for 630 nanometers and 810 nanometers may select wavelengths in the ranges of 620-640 and 800-820 nanometers; wavelengths outside these ranges may be blocked or substantially attenuated. One or more embodiments may select wavelengths with filters of any desired bandwidths around the desired center wavelengths.

The reflected biophotons 113 may be absorbed by any of the cells 114 of the subject. For example, in one or more embodiments these biophotons may interact with mitochondria 115 to increase energy production in the cell, potentially providing health benefits. Radiation of wavelength 810 nanometers (and to some extent of 635 nanometers as well) may be absorbed by cytochrome c oxidase, which is a mitochondrial chromophore, as described in Gupta et. al. (referenced above in the Description of the Related Art).

Figure 1D:
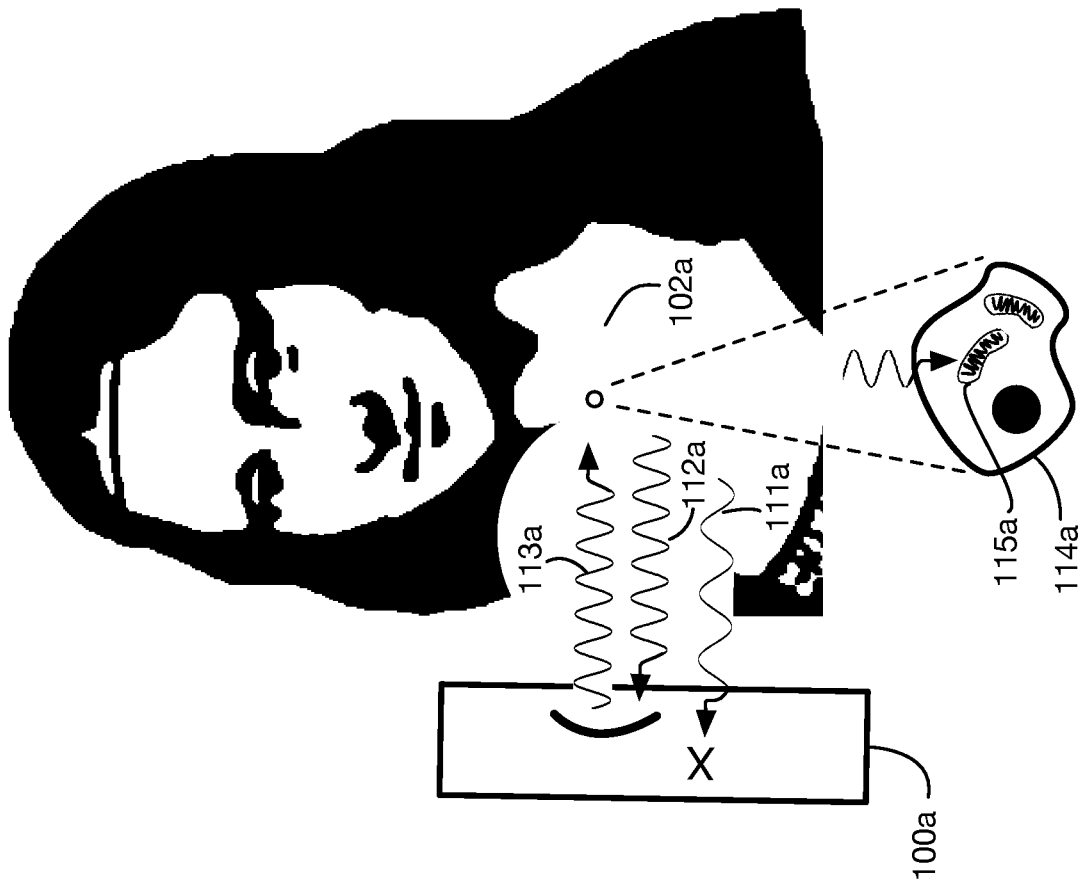
FIG. 1D shows a block diagram that illustrates the selective reflection of biophotons by the embodiment of FIG. 1C
Figure 1C:
FIG. 1C shows another illustrative embodiment of the invention worn by a subject as a pendant.

FIGS. 1C and 1D show another illustrative embodiment of the invention that may be functionally similar to the embodiment of FIGS. 1A and 1B, but is worn as a pendant instead of on the wrist. Device 100a hangs from a necklace or band 101a around the neck of subject 102a. The device may be of any size and shape. FIG. 1D shows a high-level architectural diagram of device 100a illustrating the interaction of the device with the biophotons emitted from subject 102a. The components of this architectural diagram are similar to those of the device shown in FIG. 1B: the device selectively reflects biophoton radiation 112a of a desired wavelength, resulting in reflected biophotons 113a that are directed back towards the skin of the subject 102a; other wavelengths such as biophotons 111a are not reflected. As with the device 100 of FIGS. 1A and 1B, in one or more embodiments of pendant 100a reflected biophotons may for example be absorbed by mitochondria 115a of cells 114a of the subject, increasing energy production or producing other health benefits.

FIG. 2 shows an exploded view of illustrative components of embodiment 100. The shape and size of these components may vary across embodiments. Some embodiments may have only a subset of these components. FIG. 2 also shows how illustrative biophoton waves 111, 112, and 212 interact with these components. Components to the right of the figure are closer to the skin of subject 102 when the device 100 is worn. Embodiment 100 has a housing that contains or holds the other components; in this embodiment the housing has a front portion 201a and a back cap 201b that is attached to the front portion. (In this discussion, the front of the device is the side closest to the subject's skin when work, and one component is behind another component if it is further from the subject's skin.) Housing parts 201a and 201b may be for example plastic and may be 3D printed. A clear window 202 is at the front (closest to the skin of subject 102); this window may protect the other components and may pass the biophoton wavelengths of interest with minimal attenuation. An illustrative material that may be used in one or more embodiments for the window 202 is Gorilla Glass® of thickness 1.1 mm, which transmits wavelengths between 350 nanometers and 2200 nanometers. Behind window 202 is a polarizing filter 203; this polarizer may or may not be present in one or more embodiments. Polarizer 203 may be for example a polarizing film that is coupled to the front or back of clear window 202, or to the front or back of filter 204 (described below). The polarizer, when present, selects for waves of a particular polarity. For example, waves 111 and 112, which vibrate in the plane of the page of the figure, may be passed through polarizer 203 unchanged; wave 212, which vibrates in a plane orthogonal to the plane of the page, may be blocked by polarizer 203. In some applications selecting for biophoton waves of a particular polarity may enhance effectiveness of the device.

Behind polarizer 203 is a filter 204 that may select for specific wavelengths or wavelength ranges. (In one or more embodiments, the filter 204 may be in front of polarizer 203 instead of behind it as shown in FIG. 2; in either case incoming light is both polarized and filtered.) In this example, filter 204 blocks wave 111, but passes wave 112 through the filter. An illustrative filter that may be used in one or more embodiments is for example Edmunds Optics filter #67-916, with Central Wavelength (CWL) of 810 nanometers, and a bandwidth (FWHM—full wave half maximum) of 10 nanometers. This filter may be appropriate when 810 nanometers is the desired wavelength to reflect; other applications may use different filters that select for other wavelengths. One or more embodiments may combine multiple filters to obtain a set of desired wavelengths.

Behind filter 204 is a mirror 205. This mirror reflects the waves that have passed through polarizer 203 and filter 204 back towards the subject's skin. In the example shown in FIG. 2, wave 112 is reflected to wave 113 that returns to the subject through the other components. In one or more embodiments, mirror 205 may be for example a parabolic mirror that reflects incoming waves to a common direction parallel to the central axis of the device, ensuring that waves emitted at varying angles from the skin are reflected back into the body. In one or more embodiments the parabolic mirror may be approximately parabolic; for example, it may be spherical. Mirror 205 may be a gold-coated parabolic mirror in one or more embodiments. One or more embodiments may use for example Edmunds Optics protected gold spherical mirror #32-813. In one or more embodiments the mirror may reflect a broad spectrum of wavelengths that includes the wavelengths selected by the filter. For example, the Edmunds Optics mirror described above reflects at least wavelengths in the range of 700 nanometers to 10,000 nanometers.

One or more embodiments of the invention may use multiple filters to select multiple wavelengths of biophotons that are reflected towards the user's body. This approach may be valuable when the desired beneficial effects can be generated or enhanced with more than one band of wavelengths. FIG. 3 shows an illustrative embodiment of a device 100b with multiple filters. The device is shown in an exploded view similar to the view of device 100 in FIG. 2. The window 202, polarizer 203 (if used), and back cap 201b may be identical to or similar to the equivalent components in device 100 of FIG. 2. Instead of a single filter like filter 204 of device 100, device 100b has three filters 204a, 204b, and 204c that select different associated wavelengths 311a, 311b, and 311c, respectively. Illustrative wavelengths may be for example 550 nanometers for wavelength 311a, 694 nanometers for wavelength 311b, and 632 nanometers for wavelength 311c. Illustrative filters that may be used in one or more embodiments may include for example: for filter 204a, Edmunds Optics filter #65-644, CWL 550 nm, FWHM 10 nm, diameter 12.5 mm; for filter 204b, Edmunds Optics filter #65-660, CWL 694 nm, FWHM 10 nm, diameter 12.5 mm; and for filter 204c, Edmunds Optics filter #65-711, CWL 632 nm, FWHM 10 nm, diameter 25 mm. The front cap 201c has three openings 301a, 301b, and 301c that correspond to filters 204a, 204b, and 204c, respectively. Mirror 205b may be identical to or similar to mirror 205 of FIG. 2; alternatively, in one or more embodiments mirror 205b may be for example an aluminum coated concave mirror such as Edmund Optics mirror #43-471, which reflects wavelengths between 400 nanometers and 2000 nanometers. The arrangement, shapes, sizes, and number of filters shown in FIG. 3 are illustrative; one or more embodiments may use any number of filters in any configuration to select for any desired combination of wavelengths.

In one or more embodiments, it may be beneficial to use the wearable selective biophoton reflector with one or more oral supplements that elevate one or more of Glutathione and Nitric Oxide to further enhance mitochondrial function. However, the biophoton reflector may be used with or without oral supplements.

While the invention herein disclosed has been described by means of specific embodiments and applications thereof, numerous modifications and variations could be made thereto by those skilled in the art without departing from the scope of the invention set forth in the claims.

What is claimed is:

1. A wearable selective biophoton reflector configured to be worn by a subject to provide a beneficial effect for the subject, said wearable selective biophoton reflector comprising:
    a clear window configured to be placed proximal to a body of said subject closest to a skin of said body of said subject;
    one or more filters behind said clear window,
        said one or more filters configured to selectively pass one or more biologically beneficial wavelengths from various wavelengths of biophoton radiation emitted from said body;
    a mirror behind said one or more filters,
        said mirror configured to reflect said one or more biologically beneficial wavelengths of biophoton radiation that are selectively passed back towards said skin of said body; and,
    a housing configured to hold said clear window, said one or more filters, and said mirror;
    wherein said housing comprises a front portion and a back cap attached to the front portion;
    wherein said front portion comprises one or more openings that each correspond to said one or more filters respectively,
    wherein said housing is further configured to be integrated with a wearable accessory or an article of clothing to hold said housing near or against said skin of said body of said subject via said wearable accessory or said article of clothing; and
    wherein said wearable selective biophoton reflector
        does not comprise a power source
        and
        is not coupled to any external power source.

2. The wearable selective biophoton reflector of claim 1, wherein said beneficial effect comprises elevated energy production in cells of the subject.

3. The wearable selective biophoton reflector of claim 2, wherein said beneficial effect comprises elevated energy levels of cytochrome c oxidase in said cells of the subject.

4. The wearable selective biophoton reflector of claim 1, wherein said one or more biologically beneficial wavelengths comprise one or more of 550 nanometers, 630 nanometers, 632 nanometers, 660 nanometers, 694 nanometers, 810 nanometers, and 980 nanometers.

5. The wearable selective biophoton reflector of claim 1, wherein said mirror comprises a parabolic mirror.

6. The wearable selective biophoton reflector of claim 5, wherein said mirror comprises a gold-coated mirror.

7. The wearable selective biophoton reflector of claim 1, further comprising: a polarizer between said clear window and said mirror.

8. The wearable selective biophoton reflector of claim 1, wherein said one or more filters comprise three or more filters.

9. The wearable selective biophoton reflector of claim 8, wherein said one or more biologically beneficial wavelengths of biophoton radiation comprise
    550 nanometers passed by a first filter of said three or more filters;
    632 nanometers passed by a second filter of said three or more filters; and,
    694 nanometers passed by a third filter of said three or more filters.

10. A wearable selective biophoton reflector configured to be worn by a subject to provide a beneficial effect for the subject comprising elevated energy production in cells of the subject, said wearable selective biophoton reflector comprising:
    a clear window configured to be placed proximal to a body of said subject closest to a skin of said body of said subject;
    one or more filters behind said clear window, said one or more filters configured to selectively pass one or more biologically beneficial wavelengths from various wavelengths of biophoton radiation emitted from said body,
   wherein said one or more biologically beneficial wavelengths comprise one or more of 550 nanometers, 630 nanometers, 632 nanometers, 660 nanometers, 694 nanometers, 810 nanometers, and 980 nanometers;

a gold-coated parabolic mirror behind said one or more filters,
   said gold-coated parabolic mirror configured to reflect said one or more biologically beneficial wavelengths of biophoton radiation that are selectively passed back towards said skin of said body;

a polarizer between said clear window and said gold-coated parabolic mirror; and a housing configured to hold said clear window, said one or more filters, said gold-coated parabolic mirror, and said polarizer;

wherein said housing comprises a front portion and a back cap attached to the front portion;

wherein said front portion comprises one or more openings that each correspond to said one or more filters respectively;

wherein said housing is further configured to be integrated with a wearable accessory or an article of clothing to hold said housing near or against said skin of said body of said subject via said wearable accessory or said article of clothing; and, wherein said wearable selective biophoton reflector
   does not comprise a power source
      and
      is not coupled to any external power source.

\* \* \* \* \*